United States Patent [19]

Colle et al.

[11] Patent Number: 4,468,243

[45] Date of Patent: Aug. 28, 1984

[54] HERBICIDES

[75] Inventors: Roberto Colle, Milan; Franco Gozzo, S. Donato Milanese; Ciro Preziuso, Milan, all of Italy

[73] Assignee: Montedison S.p.A., Milan, Italy

[21] Appl. No.: 356,420

[22] Filed: Mar. 9, 1982

Related U.S. Application Data

[63] Continuation of Ser. No. 159,957, Jun. 16, 1980, abandoned.

[30] Foreign Application Priority Data

Jun. 15, 1980 [IT] Italy ............................... 23621 A/79

[51] Int. Cl.$^3$ ..................... A01N 41/12; C07C 149/42
[52] U.S. Cl. ............................................ 71/88; 71/94; 71/98; 260/453 RW; 544/85; 546/191; 546/243
[58] Field of Search .......................... 544/85; 546/191; 564/243; 260/453 RW; 71/88, 94, 98

[56] References Cited

U.S. PATENT DOCUMENTS 2,843,628 7/1958 Rust ................................... 564/243

OTHER PUBLICATIONS

Strivastrava et al., Tetrahedron Letters, vol. 23 (1968) pp. 2725–2726.
Strivastrava et al., J. Ind. Chem. Soc., vol. 40 (1963) pp. 803–807.
Strivastrava et al., Indian. J. Chem. vol. 1 (1963) pp. 354–358, 432–434.

*Primary Examiner*—Richard Raymond
*Attorney, Agent, or Firm*—Stevens, Davis, Miller & Mosher

[57] ABSTRACT

Formamidine sulphides and disulphides endowed with herbicide activity are disclosed.

The processes for their preparation, their use as herbicides and herbicidal compositions thereof are disclosed too.

5 Claims, No Drawings

HERBICIDES

This is a continuation of application Ser. No. 159,957 filed June 16, 1980, now abandoned.

BACKGROUND OF THE INVENTION

A restricted number of formamidine disulphides is known in literature, however herbicide properties were never recognized to such compounds.

P. K. Srivastrava and coll. prepared, for merely academical purposes, the following formamidine disulphides in the form of bromohydrates:

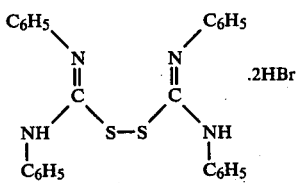

(P. K. Strivastrava et al., Tetrahedron Letters 23, 2725, 1968)

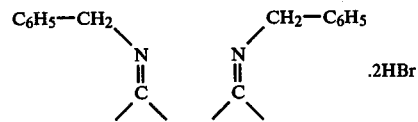

(P. V. Srivastrava et al., J. Ind. Chem. Soc. 40, 803, 1963)

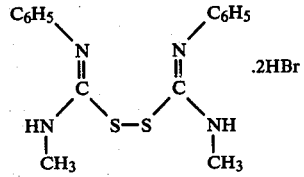

(P. V. Srivastrava et al., Indian J. Chem. 1, 354, 432, 1963)

However no analytical data for the characterization of the abovesaid three compounds are reported, probably because, due to their instability, they cannot be isolated as free bases.

THE PRESENT INVENTION

We have now found formamidine sulphides and disulphides, which are the object of the present invention, having general formula:

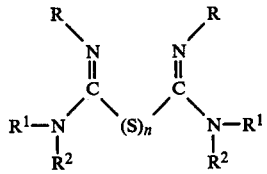

in which:
- R = phenyl optionally substituted by one or more halogen atoms, one or more alkyl or haloalkyl groups with from 1 to 3 carbon atoms;
- $R^1$ and $R^2$ (like or unlike each other) = alkyl $C_1$–$C_3$, alkoxyl $C_1$–$C_3$ or $R^1$ and $R^2$ together form an alkylidene chain having 4 or 5 carbon atoms optionally interrupted by heteroatoms;
- n = 1 or 2.

The compounds of general formula I are endowed with a high herbicide activity.

The compounds of general formula I are prepared by oxidation of trisubstituted thioureas (II) in the presence of an organic base (reaction 1), so obtaining the compounds of formula I in which n=2 (disulphides), from which, by desulphurization in the presence of triphenyl-phosphine (reaction 2), the corresponding sulphides are obtained. The same compounds can be obtained also by reacting a trisubstituted thiourea (II) with the proper imidoyl-chloride (III) in the presence of an halogenhydric acid-accepting base (reaction 3).

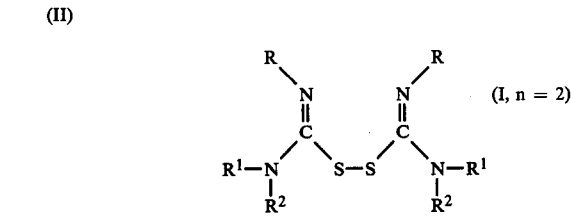

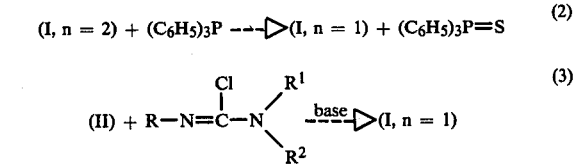

Reaction 1 is conducted by oxidizing thiourea (II) in the presence of an organic base and in an inert solvent.

As oxidizing agent it is possible to use, for example, a halogen such as bromine and iodine ($Br_2$, $J_2$), while a tertiary amine such as triethyl- or tributyl-amine can be used as an organic base.

Excellent yields were obtained by using methylene chloride ($CH_2Cl_2$) or chloroform ($CHCl_3$) as a solvent.

Under the conditions described hereinbefore the reaction occurs at room temperature and in very short times. At the conclusion of the reaction the mixture is washed with water and anhydrified, and the solvent is evaporated. The resulting product can be utilized as such, otherwise it can be crystallized from non-polar solvents.

Reaction 2 can be advantageously conducted by reacting equimolar amounts of disulphide (obtained from reaction 1) and triphenyl-phosphine, in diethylether at 0° C.

The resulting triphenyl-phosphine sulphide precipitates and is removed by filtration at the end of the reaction. The reaction mixture is treated according to usual laboratory techniques and the formamidine sulphide so obtained is purified by crystallization from hydrocarbons.

Reaction 3 directly leads to the obtainment of formamidine sulphides without preparing first the corresponding disulphides.

The reaction is conducted in an aprotic solvent and in the presence of a halogenhydric acid-accepting base.

An advantageous process for conducting the abovesaid reaction consists in adding a solution of the thiourea derivative (II) and of a slight excess of base (tertiary amine) in methylene chloride, to a solution of imidoyl chloride (III) in the same solvent.

The mixture is stirred at room temperature and the reaction occurs in a short time.

The product is then isolated according to the usual laboratory techniques.

By operating conforming to the methods described hereinbefore, the compounds of formula (I) recorded on Table I were prepared.

TABLE I

Compounds of formula

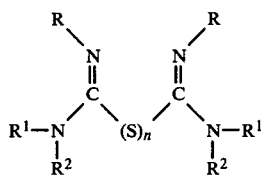

| Compound No. | n | R | R$^1$ | R$^2$ | Elemental analysis (%) theor. values | Elemental analysis (%) found values | NMR($\delta$,$^{(1)}$) ppm) | m.p.$^{(2)}$ (°C.) | IR$^{(3)}$ (cm$^{-1}$) | Rough formula M.W. |
|---|---|---|---|---|---|---|---|---|---|---|
| 1 | 1 | 4-CH$_3$—C$_6$H$_4$ | iC$_3$H$_7$ | iC$_3$H$_7$ | C 72.05<br>H 9.07<br>N 12.00 | 72.45<br>8.78<br>10.35 | 7.3–6.5 (m)<br>4–3.4 (q)<br>2.3 (s)<br>1.07–0.97 (d) | | 1610;<br>1590<br>1360–<br>1370 | C$_{28}$H$_{42}$N$_4$S<br><br>466.74 |
| 2 | 2 | 4-Cl—C$_6$H$_4$ | CH$_3$ | CH$_3$ | C 50.58<br>H 4.72<br>N 13.11 | 50.28<br>4.56<br>13.01 | | | | C$_{18}$H$_{20}$N$_4$S$_2$Cl$_2$<br><br>427.42 |
| 3 | 2 | 4-Cl—C$_6$H$_4$ | —CH$_2$—CH$_2$—O—CH$_2$—CH$_2$— | | C 51.66<br>H 4.73<br>N 10.95 | 51.66<br>4.71<br>11.06 | | 150–<br>152 | | C$_{22}$H$_{24}$N$_4$S$_2$O$_2$Cl$_2$<br><br>511.50 |
| 4 | 2 | 4-Cl—C$_6$H$_4$ | —CH$_2$—(CH$_2$)$_3$—CH$_2$— | | C 56.79<br>M 5.56<br>N 11.04 | 55.52<br>5.50<br>11.14 | | 105–<br>107 | | C$_{24}$H$_{28}$N$_4$S$_2$Cl$_2$<br><br>507.55 |
| 5 | 2 | 3,4-Cl$_2$—C$_6$—H$_3$ | CH$_2$(CH$_2$)$_3$—CH$_2$— | | C 50.00<br>H 4.55<br>N 9.72 | 49.07<br>4.41<br>9.42 | | 136–<br>138 | | C$_{24}$H$_{26}$N$_4$S$_2$Cl$_4$<br><br>576.44 |
| 6 | 2 | 3,4-Cl$_2$—C$_6$H$_3$ | iC$_3$H$_7$ | iC$_3$H$_7$ | C 51.32<br>H 5.63<br>N 9.21 | 50.32<br>5.46<br>8.21 | | 130–<br>132 | | C$_{26}$H$_{34}$N$_4$S$_2$Cl$_4$<br><br>608.53 |
| 7 | 1 | 3,4-Cl$_2$C$_6$H$_3$ | —CH$_2$—(CH$_2$)$_3$—CH$_2$— | | C 52.95<br>H 4.81<br>N 10.29 | 54.78<br>4.86<br>9.46 | | 133–<br>136 | 1590–<br>1560<br>1370–<br>1110 | C$_{24}$H$_{26}$N$_4$SCl$_4$<br><br>544.38 |
| 8 | 1 | 3,4-Cl$_2$—C$_6$H$_3$ | iC$_3$H$_7$ | iC$_3$H$_7$ | C 54.17<br>H 5.94<br>N 9.72 | 55.63<br>5.73<br>8.45 | 7.3–6.57 (m)<br>4.0–3.3 (q)<br>0.95–1.07 (d) | 160–<br>165 | 1610–<br>1570–<br>1360 | C$_{24}$H$_{34}$N$_4$SCl$_4$<br><br>576.46 |
| 9 | 2 | 3-CF$_3$—C$_6$H$_4$ | —CH$_2$—CH$_2$—O—CH$_2$—CH$_2$— | | S 11.08<br>N 9.68 | 11.15<br>9.32 | | 114–<br>115 | | C$_{24}$H$_{24}$F$_6$N$_4$O$_2$S$_2$<br><br>578.59 |
| 10 | 2 | 4-Cl—C$_6$H$_4$ | iC$_3$H$_7$ | iC$_3$H$_7$ | C 58.09<br>H 6.37<br>N 10.42 | 57.70<br>6.77<br>10.48 | | 156–<br>158 | | C$_{26}$H$_{34}$N$_4$S$_2$Cl$_2$<br><br>537.62 |
| 11 | 1 | 4-Cl—C$_6$H$_4$ | CH$_3$ | CH$_3$ | C 54.68<br>H 5.1<br>N 14.17 | 54.64<br>4.9<br>14.42 | | 107–<br>108 | 1610–<br>1590–<br>1575<br>1080 | C$_{18}$H$_{20}$N$_4$SCl$_2$<br><br>595.36 |
| 12 | 1 | 4-Cl—C$_6$H$_4$ | CH$_2$—(CH$_2$)$_3$—CH$_2$— | | C 60.62<br>H 5.93<br>N 11.78 | 62.87<br>5.84<br>9.67 | | 146–<br>151 | 1695–<br>1590<br>1570–<br>1370 | C$_{24}$H$_{28}$N$_4$SCl$_2$<br><br>475.49 |
| 13 | 1 | 4-Cl—C$_6$H$_4$ | iC$_3$H$_7$ | iC$_3$H$_7$ | C 61.77<br>H 6.78<br>N 11.08 | 63.49<br>6.90<br>9.33 | | 159–<br>165 | 1600–<br>1590<br>1570–<br>1360 | C$_{26}$H$_{36}$N$_4$SCl$_2$<br><br>505.56 |
| 14 | 2 | 3,4-Cl$_2$—C$_6$H$_3$ | —CH$_2$—CH$_2$—O—CH$_2$—CH$_2$— | | C 45.52<br>H 3.82<br>N 9.65 | 44.63<br>3.68<br>9.4 | | 123–<br>125 | | C$_{22}$H$_{22}$N$_4$S$_2$O$_2$Cl$_4$<br><br>580.38 |
| 15 | 2 | 3,4-Cl$_2$—C$_6$H$_3$ | CH$_3$ | CH$_3$ | C 43.54<br>H 3.62<br>N 11.26 | 43.68<br>3.55<br>11.15 | | 69–71 | | C$_{18}$H$_{18}$N$_4$S$_2$Cl$_4$<br><br>495.8 |
| 16 | 1 | 3,4-Cl$_2$—C$_6$H$_3$ | CH$_3$ | CH$_3$ | C 46.57<br>H 3.9<br>N 12.07 | 48.86<br>4.00<br>10.95 | 7.35–6.45 (6H, m)<br>2.73 (12H, s) | 95–97 | | C$_{18}$H$_{18}$N$_4$SCl$_4$<br><br>464.25 |
| 17 | 1 | C$_6$H$_5$ | CH$_3$ | CH$_3$ | C 66.22<br>H 6.79<br>N 17.16 | 66.2<br>6.8<br>17.25 | 7.4–6.6 (10H, m)<br>2.68 (12H, s) | 100–<br>102 | 1620–<br>1585<br>1300–750<br>690 | C$_{18}$H$_{22}$N$_4$S<br><br>326.47 |
| 18 | 2 | C$_6$H$_5$ | CH$_3$ | CH$_3$ | C 60.3 | 60.45 | 7.44–6.46 (10H, m) | | 1610–<br>1585 | C$_{18}$H$_{22}$N$_4$S$_2$ |

TABLE I-continued

Compounds of formula

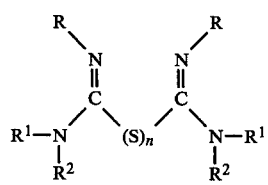

| Compound No. | n | R | R¹ | R² | Elemental analysis (%) theor. values | found values | NMR($\delta$),[1] ppm | m.p.[2] (°C.) | IR[3] (cm$^{-1}$) | Rough formula M.W. |
|---|---|---|---|---|---|---|---|---|---|---|
| | | | | | H 6.2 | 6.2 | 2.9 (12H, s) | 56–60 | 1260–1100 920–830–765–698 | 358.47 |
| | | | | | N 15.65 | 15.65 | | | | |
| 19 | 2 | 4-$CH_2$—$C_6H_4$ | $iC_3H_7$ | $iC_3H_7$ | C 67.42 | 67.53 | | 114–119 | | $C_{28}H_{42}N_4S_2$ 498.80 |
| | | | | | H 8.49 | 8.72 | | | | |
| | | | | | N 11.23 | 11.32 | | | | |
| 20 | 2 | 3-$CF_3$—$C_6H_4$ | $CH_3$ | $CH_3$ | S 12.96 | 12.46 | | oil | | $C_{20}H_{20}F_6N_4S_2$ 494.51 |
| | | | | | N 11.33 | 11.39 | | | | |
| 21 | 2 | 3-$CF_3$—$C_6H_4$ | —$CH_2$—$(CH_2)_3$—$CH_2$— | | S 11.16 | 10.23 | | oil | | $C_{26}H_{28}F_6N_4S_2$ 574.68 |
| | | | | | N 9.75 | 9.73 | | | | |
| 22 | 2 | 3-$CF_3$—$C_6H_4$ | $iC_3H_7$ | $iC_3H_7$ | S 10.57 | 10.67 | | 111–112 | | $C_{28}H_{36}F_6N_4S_2$ 606.72 |
| 23 | 1 | 3-$CF_3$—$C_6H_4$ | $CH_3$ | $CH_3$ | | | 7.45–6.85 (m) | | 1600–1590–1575– | $C_{20}H_{18}N_4F_6S$ |
| | | | | | | | 2.65 (s) | 96–100 | 1370–1320–1210 | 462.45 |
| 24 | 1 | 3-$CF_3$—$C_6H_4$ | —$CH_2$—$(CH_2)_3$—$CH_2$— | | F 21.01 | 20.10 | | | | $C_{26}H_{26}F_6N_4S$ 542.58 |
| | | | | | N 10.33 | 11.22 | | oil | | |
| 25 | 1 | 3-$CF_3$—$C_6H_4$ | $iC_3H_7$ | $iC_3H_7$ | | | | 130–133 | 1605–1565–1370–1360–1320–1255–1220 | |

Notes to Table I:
[1] The N.M.R. spectra were recorded by using $CDCl_3$ as solvent and TMS as internal standard; s = singlet, d = doublet, q = quadruplet, m = multiplet;
[2] The melting points were not corrected.
[3] Only the most significant bands are reported.

The compounds of general formula I are endowed with a high herbicide activity exerted against both monocotyledons and dicotyledons.

The data relating to the activity of some representative compounds, obtained as described in example 4, are reported in the following Table II.

The herbicide activity was tested on the following weeds:

MONOCOTYLEDONS

A = *Echinochloa crusgalli*
B = *Avena fatua*
C = *Lolium italicum*
D = Sorghum spp.
E = *Setaria glauca*
F = *Digitaria sanguinalis*
G = *Alopecurus myosuroides*
H = *Panicum dichotomiflorum*
I = *Festuca pratense*
J = *Bromus sterilis*
K = *Poa annua*

DICOTYLEDONS

L = *Stellaria media*
M = *Ipomea purpurea*
N = *Vigna sinensis*
O = *Rumex acetosella*
P = *Galinsoga parviflora*
Q = *Convolvolus sepium*
R = *Convolvulus ariensis*
S = *Geranium dissect*
T = *Sida spinosa*
U = Brassica
V = *Gypsophila muralis*
W = *Galium aparine*.

The data relating to the herbicide activity reported on Table II are expressed using a scale of values from 0 (no herbicide activity, growth of the plant like that of the check) to 4 (death of the plant or complete stop of growth).

TABLE II

| Compound No. (see Table I) | Treatment | Dose (Kg/ha) | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|---|---|
| 2 | Pre-emergence | 6 | | | | 4 | 4 | 4 | 4 | | | | 4 | 4 | 4 | | 4 | | | 4 | 4 | | | 4 | |
|   | Post-emergence | 2 | 4 | 4 | 4 | 4 | 4 | 4 | 4 | 4 | | 4 | 4 | 4 | 4 | 4 | 4 | | | 4 | 4 | 4 | | 4 | 4 |
| 11 | Post-emergence | 2 | 4 | 4 | 4 | 4 | 4 | 4 | 4 | 4 | 4 | | 4 | 4 | 4 | 4 | 4 | | | 4 | 4 | 4 | | 4 | 4 |
| 15 | Pre-emergence | 6 | 3 | | | | | | | | | | | 4 | 3 | 3 | 4 | 4 | | | | 4 | 4 | | |
|   | Post-emergence | 6 | 4 | 4 | 4 | 4 | 4 | 4 | 4 | 4 | 4 | 4 | | 4 | 4 | 4 | 4 | | 4 | 4 | 4 | 4 | 4 | | 4 |
| 16 | Post-emergence | 6 | 4 | | | 4 | 4 | 4 | 4 | 4 | | 4 | 4 | 4 | 4 | 4 | 4 | | 4 | 4 | 4 | 4 | | 4 | 4 |
| 17 | Post-emergence | 6 | 2 | 2 | | 4 | 4 | 4 | 4 | | | | | 4 | 4 | 4 | 4 | 4 | 4 | 4 | 4 | | | 4 | 4 |
| 20 | Post-emergence | 2 | | | | | | | | | | | | 4 | 3 | 3 | 4 | | 3 | 2 | 4 | | | 4 | 2 |

Depending on the particular compound the best effectiveness of the herbicide activity is achieved by application in pre-emergence or in post-emergence, that is when the infesting weeds have not yet emerged out of the soil or when they have.

The herbicide compounds of the invention prove also to be selective with respect to usefull cultivations such as wheat, maize, soja and cotton.

For agricultural applications the active compounds are distributed on the soil as such or, preferably, in form of suitable compositions consisting of one or more of the compounds of formula I as active principle and one or more suitable carriers.

Suitable compositions include wettable powders, liquid pastes, granular formulates and so on.

Suitable carriers include, depending on the type of composition, silica, caolin, diatomaceous earths, bentonite, pomix, organic solvents or water.

In the composition may be included also additives such as surfactants, emulsifiers, thickeners and so on. A list of carriers and additives is reported on "McCutcheons—Detergent and Emulsifiers—North American and International Editions, 1977 Annual. McCutcheons Publ. Co., Glen Rock, N.J. (U.S.A.)".

The preparation of said compositions is carried out according to procedures common to the formulation praxis.

If desired in the compositions may be included also other active ingredients such as fertilizers, insecticides or fungicides.

The amount of active principle (Compounds of formula I) to be distributed on the soil depends on various factors such as the environmental conditions, the kind of agricultural cultivation to be protected from infesting weeds, the type of composition and the particular active principle.

Generally, amounts of compounds of formula I comprised between 1 and 6 Kg/ha are suitable for obtaining good results in the fight against infesting weeds, the preferred amount being of about 2-3 Kg/ha.

The following examples are given to better illustrate the present invention.

EXAMPLE 1

Preparation of $N^1,N^1$-dimethyl-$N^2$-phenyl-formamidine disulphide (Compound No. 18, Table I)

A chloroform solution of iodine (5.2 g in 100 ml) was added dropwise to a stirred solution of N,N-dimethyl-N'-phenyl-thiourea (5 g, 0.0277 moles) and triethylamine (7.5 ml) in chloroform (50 ml).

The addition was continued until the iodine colour remained persistent in the reaction mixture.

After 15 minutes the agitation was stopped and the reaction mixture was repeatedly washed with water (750 ml) and anhydrified with anhydrous $Na_2SO_4$. After removal of the solvent a yellow oil was obtained which, crystallized from n.hexane, provided 4 g of the product to be obtained.

EXAMPLE 2

Preparation of $N^1,N^1$-dimethyl-$N^2$-phenyl-formamidine sulphide (Compound No. 17, Table I)

To a solution of $N^1,N^1$-dimethyl-$N^2$-phenyl-formamidine disulphide prepared as described in example 1 (350 mg) in diethylether (2 ml) were added, under stirring - - -, 256 mg of triphenyl-phosphine, while outside cooling by means of a water and ice bath.

After conclusion of the reaction (about 3 hours), the white precipitate of triphenyl-phosphine sulphide was removed by filtration at 0° C.

The solvent was then removed under vacuum and the residue, crystallized from n.hexane, provided 112 mg of the desired product free from impurities.

EXAMPLE 3

Preparation of $N^1,N^1$-dimethyl-$N^2$-phenyl-formamidine sulphide (Compound No. 17, Table I)

A solution of N,N-dimethyl-N'-phenyl-thiourea (0.9 g) and phosgen ($COCl_2$) (2 g), in methylene chloride, was stirred for 8 hours at room temperature. After removal of the solvent under vacuum, the residue (imidoyl chloride) was dissolved in a solution of triethylamine (0.7 ml) and anhydrous methylene chloride (20 ml).

A solution of N,N-dimethyl-N'-phenyl-thiourea (0.9 g) and triethylamine (0.7 ml) in methylene chloride (20 ml) was added dropwise, under stirring and at room temperature, to the above-mentioned solution.

After an eight-hour stirring the reaction mixture was washed with water, anhydrified with anhydrous sodium sulphate, and the solvent was removed under vacuum. The residue was crystallized from petroleum ether, so obtaining 1.4 g of the desired product (yield=86%).

EXAMPLE 4

Determination of the herbicide activity

Some pots were prepared (upper diameter=10 cm, height=10 cm) which contained sandy soil, and each pot was sowed with one of the infesting weeds listed on pages 11 and 12. To each pot water was added in the amount necessary to a good sprouting of the seeds.

The pots were divided into three sets.

The first one was not treated with any herbicide and was used as a check.

The second set was treated, one day after sowing, with a hydroacetonic dispersion (20% by volume/volume) of the compounds of the invention, in order to determine the herbicide activity in the pre-emergence stage.

The third set was treated, 15 days after sowing (namely when the little plants had already reached a height of 5-10 cm, depending on the species) with a hydroacetonic dispersion (20% by volume/volume) of the compounds of this invention in order to determine the herbicide activity in the post-emergence stage.

All the pots were kept under observation in a conditioned chamber at temperatures ranging from 15° to 24° C., relative humidity=70%, photoperiod=12 hours, light intensity=2500 lux.

Every second day all the pots were uniformly watered in order to secure a humidity degree sufficient for a good growth of the plants. 28 days after the treatment, controls were carried out to ascertain the vegetative stage of the plants, the results thereof being expressed according to the scale of values from 0 (growth equal to the one of the check) to 4 (full stop of the growth or complete killing of the plants).

What we claim is:

1. A compound stable as a free base and having the formula:

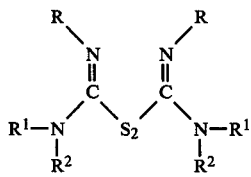

wherein R is phenyl optionally substituted by one or more halogen atoms, one or more alkyl or haloalkyl groups with from 1 to 3 carbon atoms;

$R^1$ and $R_2$ are the same or different and each represents an alkyl $C_1$-$C_3$, an alkoxyl $C_1$-$C_3$, or $R^1$ or $R^2$ together with the nitrogen atom to which they are bonded form a piperidino or morpholino radical.

2. Compounds according to claim 1, in which $R^1$ and $R^2$ (like or unlike each other)=an alkyl $C_1$-$C_3$.

3. Compounds according to claim 1, in which $R^1$, and $R^2$ together=$-CH_2-(CH_2)_3-CH_2-$; or $-CH_2-CH_2-O-CH_2-CH_2-$.

4. Herbicide compositions having, as active principle, one or more of the compounds as defined in claim 1, plus an inert carrier.

5. A method of fighting infestations of monocotyledons and dicotyledons, characterized in that one or more compounds, either as such or in the form of suitable compositions, are spread on the soil prior to or after the emergence of the plants from the soil, said compounds having the formula:

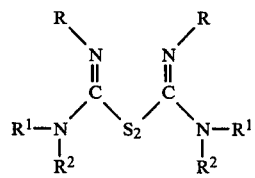

wherein

R is phenyl optionally substituted by one or more halogen atoms, one or more alkyl or haloalkyl groups with from 1 to 3 carbons;

$R^1$ and $R^2$ are the same or different and each represents an alkyl $C_1$-$C_3$, an alkoxyl $C_1$-$C_3$, or $R^1$ or $R^2$ together with the nitrogen atom to which they are bonded form a piperidino or morpholino radical.

* * * * *